Figure 1:
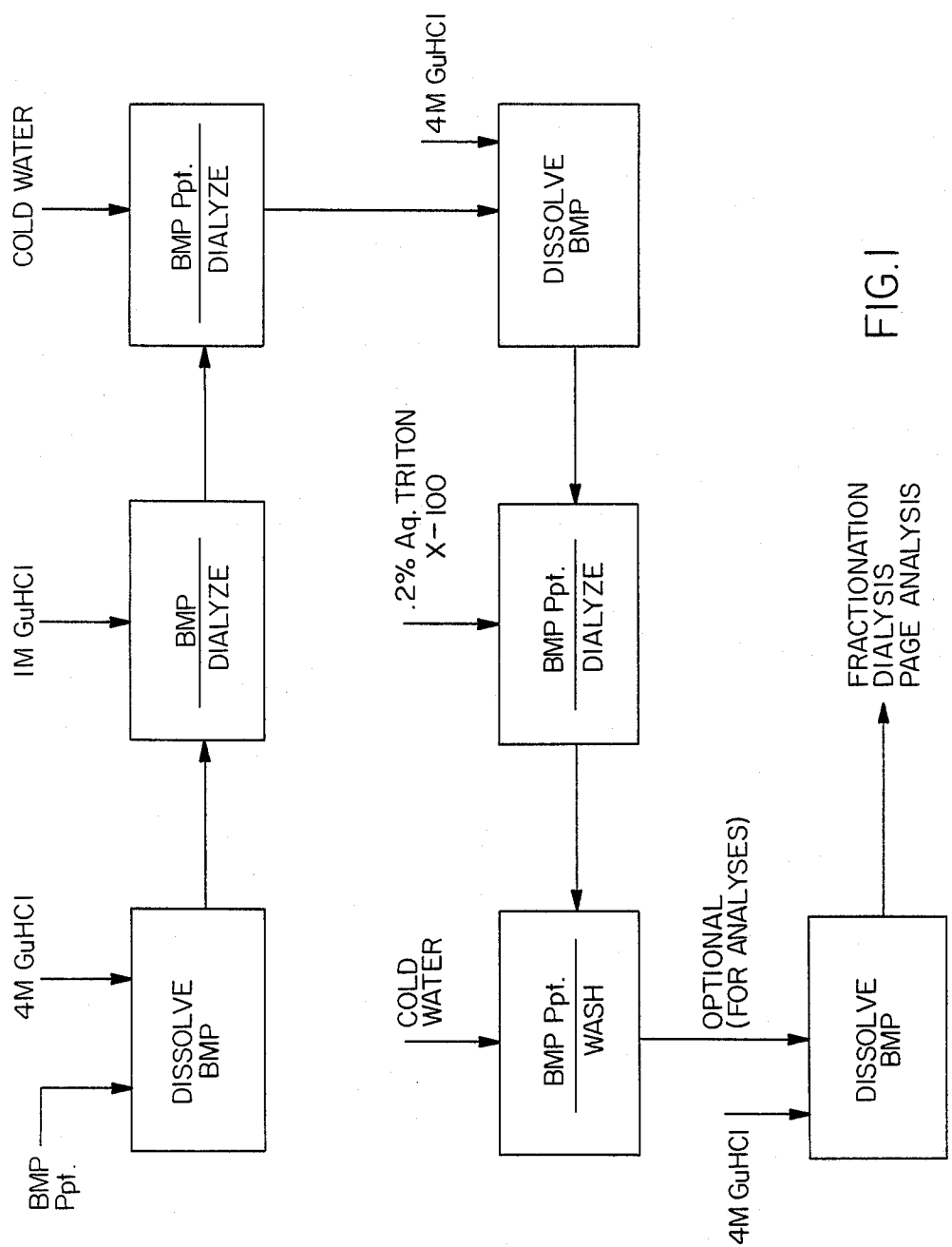

United States Patent [19]

Urist

[11] Patent Number: 4,761,471

[45] Date of Patent: Aug. 2, 1988

[54] BONE MORPHOGENETIC PROTEIN COMPOSITION

[75] Inventor: Marshall R. Urist, Pacific Palisades, Calif.

[73] Assignee: The Regents of the University of California, Berkley, Calif.

[21] Appl. No.: 899,020

[22] Filed: Aug. 22, 1986

Related U.S. Application Data

[60] Division of Ser. No. 523,606, Aug. 16, 1983, Pat. No. 4,619,989, which is a continuation-in-part of Ser. No. 260,726, May 5, 1981, Pat. No. 4,455,256, which is a continuation of Ser. No. 174,906, Aug. 4, 1980, Pat. No. 4,294,753.

[51] Int. Cl.$^4$ .......................... C07G 7/00; C07K 15/06
[52] U.S. Cl. .................................... 530/350; 530/417; 530/840; 424/95

[58] Field of Search ............... 530/350, 417, 840, 355; 424/95

[56] References Cited

PUBLICATIONS

Urist et al., "A Soluble Bone Morphogenetic Protein Extracted from Bone Matrix with a Mixed Aqueous and Nonaqueous Solvent", *Proc. Soc. Exp. Bio. and Med.*, 162, 48–53 (1979).

*Primary Examiner*—Delbert R. Phillips
*Assistant Examiner*—Nathan M. Nutter
*Attorney, Agent, or Firm*—Kenyon & Kenyon

[57] ABSTRACT

BMP compositions including the human factor and bovine factor thereof, the process of isolating BMP compositions and factors, and the use of such factors and compositions to induce bone formation in animals.

13 Claims, 2 Drawing Sheets

BONE MORPHOGENETIC PROTEIN COMPOSITION

The invention described herein was made in the course of work under a grant or award from the Department of Health and Human Services.

This is a division of copending application Ser. No. 523,606, filed Aug. 16, 1983, and now U.S. Pat. No. 4,619,989, which is a continuation-in-part application of copending application Ser. No. 260,726, filed May 5, 1981, and now U.S. Pat. No. 4,455,256, which is a continuation application of application Ser. No. 174,906, filed Aug. 4, 1980, now U.S. Pat. No. 4,294,753.

In the copending application and patent there are disclosed and claimed a process, (and the product of that process), for separating bone morphogenetic protein (BMP) from bone tissue. The process steps comprise demineralizing bone tissue; treating the demineralized bone tissue under aqueous conditions with a water soluble neutral salt and a solubilizing agent for the BMP, the agent being selected from the group consisting of urea and guanidine, and thereby transforming the bone collagen to gelatin and extracting BMP into the solution of solubilizing agent; and separating the solubilizing agent and neutral salt from the solution, thereby precipitating BMP in the aqueous medium.

A freeze dried coprecipitate of BMP with calcium phosphate, made by the aforementioned process of said patent may be implanted in a bone defect caused by injury, old infection, malignancy, and congenital defects. In the form of a freeze dried coprecipitate with calcium phosphate, 1 to 50 milligram of BMP (depending on the size of the defect) is implanted in a bone defect in which it stimulates differentiation of connective tissue into bone and thereby repairs the defect. Within about three weeks of implantation grossly visible evidence of new bone is noted. After about six months remodeling has been substantially complete and about 1 gram of bone is produced for each milligram of BMP implanted.

The molecular weight of the BMP was also described as being found to range between about 20,000 and about 63,000. Work with BMP material isolated from rabbit dentin matrix protein fraction, using polyacrylamide gel electrophoresis (PAGE) has been assigned a molecular weight of about 23,000. Since the 63,000 molecular weight preparation was prepared from osteosarcoma cells, while the 23,000 molecular weight preparation was obtained from cell free dentin matrix, it is possible that the high molecular weight form may be a proBMP and a low molecular weight form may be BMP.

The disclosures in said U.S. Pat. No. 4,294,753 and application Ser. No. 260,726 are hereby incorporated into this specification.

The present invention provides an improved process for further purifying and isolating BMP to provide the new BMP composition, namely, the BMP factor and associated proteins. The BMP composition, BMP factor and associated proteins have been determined from the purified new BMP composition, and are described and claimed herein. These materials have been isolated, and chemical and physical properties have been determined.

Basically, the process of this invention comprises purifying and isolating the new BMP composition by the steps of further purifying the BMP obtained by the process of the aforementioned patent and application. The further process steps begin with the precipitate formed when the urea (or guanidine) solution has been dialyzed against water. With reference to the Example 1 of said patent, the precipitate formed during dialysis against water is that point in the process described up to column 5, line 57 of the patent. This is also shown in the drawing as the 8th process box wherein water is added to the BMP/urea solution and dialyzed against water to remove urea, $CaCl_2$ and other impurities, thereby providing a BMP precipitate.

According to the present invention, BMP precipitate is further purified to provide the new BMP composition by dissolving BMP in guanidine hydrochloride, (preferably 4 molar solution) and sequentially dialyzing BMP solution against a less concentrated guanidine hydrochloride solution (preferably 1 molar solution), and then cold water which precipitates BMP. BMP may be redissolved in the concentrated guanidine hydrochloride and dialyzed against a dilute detergent solution to precipitate the new BMP composition.

As shown in FIG. 1 of the drawings, the BMP precipitate that was formed at this point in the prior process is dissolved in 4 molar guanidine hydrochloride, and then first dialyzed against 1 molar guanidine hydrochloride. The supernatant is then dialyzed against cold water several times; a precipitate is formed which is redissolved in 4 molar guanidine hydrochloride and dialyzed against a dilute (about 0.2%) aqueous solution of the detergent Triton X-100 during which step a precipitate is again formed. The precipitate is washed several times with cold water and may be redissolved in 4 molar guanidine hydrochloride. The solution may then be fractionated, dialyzed and analyzed by PAGE. Urea may also be used in place of guanidine.

Molecular BMP composition is isolated in the form of its water insoluble precipitate that is formed after removal of guanidine hydrochloride. Insolubility is attributable to a 14-kilo Dalton (kDa) molecular weight protein that coprecipitates with BMP. The insoluble aggregate has been converted to soluble BMP by removing the 14-kDa protein by ultrafiltration.

The coprecipitated proteins are prepared for analysis by incubation in a phosphate buffer containing urea and sodium dodecyl sulphate (SDS) at a pH of about 7.2. Thereafter the BMP preparation is analyzed for molecular weight determinations using PAGE. Small samples of the incubated BMP composition are applied to the gel, electrophoresed, and stained. The gels are sliced across zones corresponding to various molecular weights of the proteins and analyzed. Gel slices are analyzed for amino acid content and sequences. Molecular weight zones are sliced through the gel in areas, ranging between about 14-kDa and 34-kDa.

Under the influence of the new BMP composition, perivascular mesenchymal type cells (pericytes) differentiate into cartilage and woven bone within 7 days, woven bone in 14 days, and lamellar bone in 21 days.

BMP factor is an acidic protein embedded in a complex assortment of intra- and extracellular protein aggregates derived from dentin, bone and osteosarcoma tissues. BMP composition is solubilized under dissociative conditions by either a $CaCl_2$/urea inorganic-organic solvent mixture, or 4M GuHCl, or the two solvents in sequence.

Table 1 discloses the amino acid composition of a 17.5±0.5-kDa protein isolated and purified in accordance with this invention from human femoral and tibial cortical bone obtained soon after death. This protein has been determined to be the active protein factor of BMP derived from human bone sources and is referred to herein a human BMP (hBMP) factor. It is a component of the associated proteins that form human BMP composition.

TABLE 1

AMINO ACID ANALYSIS OF hBMP FACTOR ISOLATED BY SDS EXTRACTION OF PAGE SLICES

| Amino Acids | Nanomoles* | Mole % | Residue Weight 17,000 | Mole Protein |
|---|---|---|---|---|
| Lys | 2.05 | 4.09 | 7.16(7) | 897.19 |
| His | 0.83 | 1.66 | 2.91(3) | 411.42 |
| Arg | 3.51 | 7.00 | 12.25(12) | 1874.16 |
| Asp | 4.00 | 7.98 | 13.97(14) | 1611.12 |
| Thr | 1.54 | 3.07 | 5.37(5) | 505.50 |
| Ser* | 4.03 | 8.04 | 14.07(14) | 1218.98 |
| Glu | 5.10 | 10.17 | 17.80(18) | 2323.98 |
| Pro | 1.86 | 3.71 | 6.49(6-7) | 582.66 |
| Gly | 12.45 | 24.83 | 43.45(43) | 2453.15 |
| Ala | 3.40 | 6.78 | 11.87(12) | 852.84 |
| ½ Cys* | 0.98 | 1.95 | 3.41(3-4) | 309.42 |
| Val* | 2.20 | 4.39 | 7.68(8) | 793.04 |
| Met | 0.48 | 0.96 | 1.68(2) | 262.38 |
| Ileu* | 1.55 | 3.09 | 5.41(6) | 678.90 |
| Leu | 3.40 | 6.78 | 11.87(12) | 1357.80 |
| Tyr | 1.45 | 2.89 | 5.06(5) | 815.85 |
| Phe | 1.31 | 2.61 | 4.57(5) | 735.85 |
| | 50.14 | 100.00 | 175–177 + Trp + $(CH_2O)X$ | 17,684 + Trp + $(CH_2O)X$ |

*Nanomoles for each amino acid equals the average of 24- and 72-hour hydrolysates or the extrapolated value (Ser) or the 72-hour value only (Val and Ileu) or the value from the hydrolysate of the performic acid-oxidized sample (½ Cys). The margin of accuracy was about ±3%.

Serine, aspartic acid, glutamic acid and glycine are the predominant amino acids. The molecular weight calculation, based upon the sum of the individual weights of amino acids (not including tryptophan) is approximately 17,684. The total carbohydrate contents in the BMP composition is approximately 12% of the combined fractions with none detectable in the 17.5-kDa hBMP factor.

Variable quantities of other relatively low molecular weight proteins found in the human BMP composition with assigned molecular weights of 14-, 22-, 24-, and 34-kDa are dissassociated from hBMP by differential precipitation, or in some instances by ultrafiltration. Each of the associated proteins can be removed from hBMP without loss of BMP activity. However, the isolated 17.5-kDa hBMP factor is more rapidly adsorbed by tissue than the aggregates of 17.5-kDa hBMP factor and the other associated proteins, and must be implanted in greater quantities to produce the same yield of new bone. In one example, the bovine BMP (bBMP) factor which was isolated and purified as described herein, and which had an assigned molecular weight of 18.5±0.5-kDa, yielded approximately 1 gram of new bone for each milligram of bBMP implanted in the absence of the other proteins. The isolated BMP factor induces a lower yield of bone when implanted in the absence of the associated proteins.

bBMP factor is an 18.5±0.5-kDa molecular weight molecule derived from a non-collagenous protein aggregate that induces differentiation of mesenchymal type cells into cartilage and bone. bBMP factor is difficult to separate from insoluble proteins associated therewith that have assigned molecular weights of 34-, 24-, 22-, 17.5-, 17.0-, 16.5-, and 14-kDa and which may include traces of ferritin. The bBMP aggregate becomes soluble in aqueous media when it is separated from the 14-kDA protein by ultrafiltration. (For example, 2 liter batches of $CaCl_2$/urea soluble bovine BMP composition in 0.01M phosphate buffer, pH 7, were processed through an H1 P-10-8 hollow fiber cartridge (Amicon), 10-kDa approximate cutoff.) The 34-kDa protein is separated by extraction with Triton X-100. In the absence of 34-kDa, the 22-kDa is collected in the unbound fraction by hydroxyapatite chromatography. The 24- and 22-kDa proteins are separated by precipitation in 1.0–1.5M GuHCl. BMP fractions produced an electrophoretic pattern with a broad band for proteins with an assigned molecular weight of 17- to 18-kDa. Further resolution of these proteins by means of hydroxyapatite chromatography produces three components with apparent molecular weights of 18.5-, 17.5-, and 17.0-kDa. Although relatively small in quantity (<0.001 percent of the wet weight of cortical bone), the isolated 18.5±0.5-kDa protein induces bone formation independent of other matrix components. The 34-, 24-, 22-, 17.5-, 17.0-, 16.5-, and 14-kDa components do not induce bone formation. The 17.5-kDa has the N-terminal amino acid sequence of histone H2B. Insofar as the N-terminal amino acid was unblocked, the 17.5-kDa associated BMP (bovine) derived from bBMP composition was selected for amino acid sequencing. The first 26 amino acids are in the following sequence: Pro GlutA Pro Ala Lys Phe Ala Pro Ala Pro[10] Lys Lys Gly Phe Lys Lys Ala Val Tyr (Tyr)[20] Ala GluN (lys) Asp (Phe)[26].

The 18.5-kDa bBMP has a block N-terminal amino acid.

Table 2 shows the amino acid analyses (±3%) of bBMP factor (18.5-kDa) and its 22-, and 14-kDa associated protein fractions.

TABLE 2

AMINO ACID ANALYSIS OF BOVINE BMP

| Amino Acid | 22-kDa Mole % | Residues 200 | 18.5-kDa Mole % | Residues 180 | 14-kDa Mole % | Residues 130 |
|---|---|---|---|---|---|---|
| Lys | 2.83 | 6 | 9.6 | 10 | 4.46 | 6 |
| His | 2.35 | 5 | 3.4 | 3 | 1.70 | 2 |
| Arg | 6.04 | 12 | 16.6 | 17 | 9.23 | 12 |
| Asp | 12.29 | 26 | 16.8 | 17 | 11.40 | 15 |
| Thr | 3.64 | 7 | 7.1 | 7 | 2.57 | 3 |
| Ser | 5.43 | 11 | 17.6 | 18 | 6.58 | 9 |
| Glu | 14.54 | 29 | 23.4 | 23 | 14.84 | 19 |
| Pro | 6.58 | 13 | 9.0 | 9 | 5.08 | 7 |

TABLE 2-continued
AMINO ACID ANALYSIS OF BOVINE BMP

| Amino Acid | 22-kDa Mole % | Residues 200 | 18.5-kDa Mole % | Residues 180 | 14-kDa Mole % | Residues 130 |
|---|---|---|---|---|---|---|
| Gly | 8.71 | 17 | 12.4 | 12 | 6.14 | 8 |
| Ala | 5.99 | 12 | 14.4 | 14 | 8.56 | 11 |
| ½ Cys | 3.74 | 7–8 | — | — | 2.06 | 3 |
| Val | 4.51 | 9–10 | 11.0 | 11 | 3.88 | 5 |
| Met | 2.21 | 4–5 | 2.75 | 3 | 1.30 | 2 |
| Ileu | 2.67 | 5–6 | 5.9 | 6 | 4.09 | 5–6 |
| Leu | 6.27 | 14 | 15.0 | 15 | 7.54 | 10 |
| Tyr | 8.30 | 17 | 7.8 | 8 | 6.59 | 9 |
| Phe | 4.10 | 8 | 7.2 | 7 | 3.98 | 5 |
| Trp | N.D. | — | — | — | N.D. | — |

The isolated and purified hBMP factor that possesses bone induction activity has the properties shown in Table 3.

TABLE 3
PHYSIOCHEMICAL PROPERTIES OF hBMP Factor

Apparent MW 17.5 ± 0.5-kDa.
Acidic Polypeptide.
Binds to hydroxyapatite.
Isoelectric point (pI) 5.0 ± 0.2.
Carbohydrate, none detected.
Soluble in neutral salt solution at pH 7.2.
Degraded by acid alcohol solutions.
Alkali sensitive.
Insolubilized by forming aggregates with associated 14-kDa proteins.
Contains carboxyglutamic acid, about 3 residues/170 residues.
May contain hydroxyproline.
Insoluble in chloroform, methanol, absolute alcohol, acetone.
BMP 14-kDa complex with hBMP factor: insoluble in Triton X-100 (non-ionic detergent); insoluble in 0.6 N HCl; soluble in 6 M urea or 4 M guanidine HCl; soluble in 0.1% SDS; soluble in 0.02 N HCl; and partially soluble in ethylene glycol.
Trypsin and chymotrysin labile.
Resistant to: chondroitinases A, B, and C; amylase; neuroamidase; hyaluronidase; alkaline phosphates; acid phosphatase; chymopapain; collagenase; tyrosinase; thermolysin; and nuclease (RNAase and DNAase).
Partially degraded by pepsin and papain.

Monoclonal human anti-BMP immunologically cross reacts with bovine anti-BMP.

In vivo, hBMP factor is soluble enough to diffuse through as many as 5 membranes, each 125 micrometers in thickness, pore size 0.45 micrometers, or two such membranes with pores sizes of only 250 Å.

As described above, the hBMP and bBMP factors have the biochemical characteristics of a relatively insoluble polypeptide that is closely associated with the other equally insoluble low-molecular weight, electrophoretically defined associated proteins. The 34-kDa protein is a Triton X-100-soluble, water-soluble glycoprotein that is relatively easy to separate in large quantities. The 24- and 14-kDa components are difficult to separate from each other and from the 17.5-kDa hBMP (or 18.5-kDa bBMP) by differential precipitation, gel filtration, and preparative gel electrophoresis. The 17.5-kDa hBMP (or 18.5-kDa bBMP) are invariably present in chromatographic fractions having high BMP activity, and are generally absent in protein fractions lacking BMP activity. The isolated 34-, 24-, 22- and 14-kDa associated proteins do not induce bone formation. The 17.5-kDa protein from human bone and the 18.5-kDa protein from bovine bone are therefore believed to be the putative BMP factors.

Figure 2:
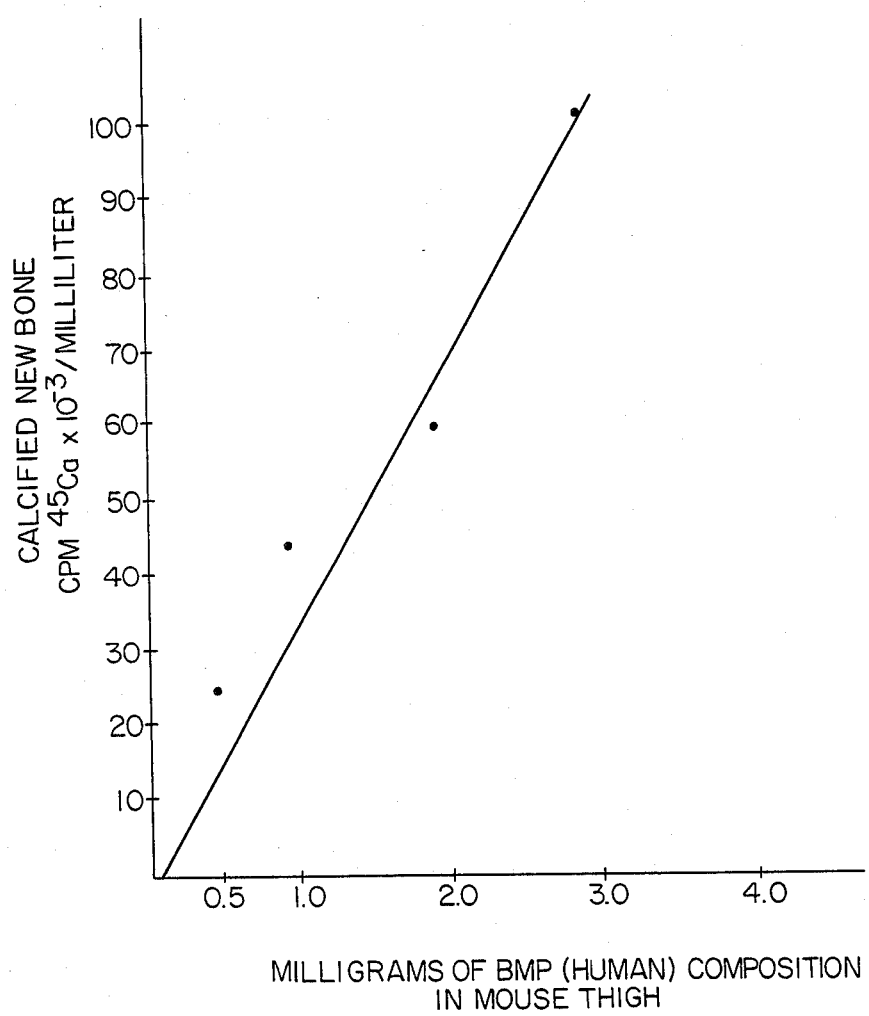

The dose-response curve to implants to BMP (human) composition, prepared by the procedure described herein, is shown in the accompanying FIG. 2 of the drawings. The yield of calcified new bone is shown to be in direct proportion to the quantity of BMP (human) composition implanted in muscle in the mouse thigh. The incorporation of $^{45}Ca \times 10^{-3}$/ml. into histologically valid deposits of new bone was directly proportional to the weight of implanted BMP (human) composition, ranging from 22 to 102 cpm $^{45}Ca \times 10^{-3}$/ml. In contrast, the unimplanted contralateral muscle emitted only 3 cpm. The correlation coefficient of the BMP (human) composition to induced bone formation was 0.9924. Control implants of human tendon collagen and serum albumin invariably failed to induce bone formation.

Since implants of about 1.0 mg of the isolated 17.5-kDa hBMP factor induce formation of hardly detectable volumes of bone, and since 1.0 mg of such BMP compositions that include the 24- and 14-kDa proteins may serve either as carriers or distributors of the biologically active 17.5-kDa hBMP or 18.5-kDa bBMP, induction by the 24- and 14-kDa proteins may be due to the spacial relationship among the various fractions of the BMP compositions and particularly with respect to their spacial relationship to the components of the cell upon which the BMP composition acts to induce the formation of bone. However, the biochemical interactions of highly complex extra- and intracellular processes leads to generation of an entire embryonic type bone morphogenetic program. Consequently, either indirectly or directly, BMP activates DNA sequences that code for bone morphogenesis. BMP is a morphogen that activates a new DNA sequence.

It is theorized that the BMP factor and the other associated proteins isolated from bone matrix gelatin are joined in a spacial relationship on a receptor of the surface of a cell. It is believed that the bond between 24- and 34-kDa proteins is severed by 4M GuHCl. Likewise, the 22- and 24-kDa proteins are isolated by differential precipitation in 1.0M GuHCl, and the bond between the 17.5-kDa hBMP or 18.5-kDa bBMP and the 34-kDa protein is severed by extraction with Triton X-100. The 17.5-kDa hBMP and the 14-kDa proteins are thought to be disassociated in 4M GuHCl, and may be separated by ultrafiltration. The BMP factor is isolated by gel filtration, preparative gel electrophoresis, and hydroxyapatite chromatography.

1 to 3 milligrams of the purified BMP compositions are required to induce grossly visible bone formation, and the yield is proportional to the mass of implanted protein. Smaller quantities are either too rapidly absorbed and excreted, or too completely degraded by tissue proteases, i.e, BMPases, to allow time for a sufficient number of mesenchymal cell populations to develop and respond.

EXAMPLE 1 hBMP was extracted from 10 kg. of femoral and tibial cortical bone obtained (within 12 hr after death) from randomly selected, male autopsy subjects, 29 to 52 years of age. The bone was frozen in liquid nitrogen, pulverized, defatted, demineralized, converted into 1.2 kg of bonematrix gelatin, and freeze-dried by methods described in said U.S. Pat. No. 4,294,753. The hBMP was isolated by the procedures shown in FIG. 1.

The water insoluble precipitate of relatively crude BMP composition was solubilized in a 6M urea solution containing 0.5M $CaCl_2$ and dialyzed against water three times. The resultant precipitate was centrifuged to remove water and redissolved in 4.0M guanidine hydrochloride. The BMP solution was then dialyzed against 1.0M guanidine hydrochloride and the supernatant was dialyzed against cold water, leaving a precipitate. The precipitate was then redissolved in 4.0M guanidine hydrochloride that was formed was washed thrice with cold water and again dissolved in 4.0M guanidine hydrochloride.

EXAMPLE 2

Ten kilogram batches of 1 year old steer long bones were obtained from abbatoire. After the epiphyseal ends were cut away with a band saw, the diaphyses were mechanically scraped clean of soft tissues, and extensively washed in a cold water solution of sodium azide (NaN$_3$), 3 mmoles/l. The washed bone was frozen in liquid nitrogen, ground in a Wiley mill to a particular size of 1 mm, defatted in 1:1 chloroform methanol, and again washed in 10 liters of cold water (Step I, see Table 4).

The bone particles were demineralized in 0.6N HCl at 4° C. for 48 hrs. and again extensively rewashed in NaN$_3$ solution (Step II). The demineralized washed bone particles were chemically extracted to remove soluble non-collagenous proteins (i.e., sialoproteins, plasma proteins, gla proteins, and phosphoproteins) simultaneously converting the collagen to insoluble bone matrix gelatin (Step III) by procedures described in U.S. Pat. No. 4,294,753. Ten kilograms of whole wet bone produced approximately 1.4 kgs. of freeze dried insoluble bone matrix gelatin.

The BMP was extracted from the insoluble bone matrix gelatin in an inorganic-organic solvent mixture of 0.5M CaCl$_2$ in 6M urea at 28° C. for 24 hrs. containing 2 mmoles/l. protect BMP against endogenous degradative enzymes.

The undissolved matrix and other substances were removed by centrifugation at 10,000 g for 30 minutes. The supernatant solution was decanted, diluted with 23 volumes of deionized water at 4° C., and allowed to stand overnight while a precipitate formed. The precipitate was collected by centrifugation (Sorvall RC-5B Refrigerated Superspeed) at 40,000 g for 20 minutes, and washed in cold deionized water, and weighed (Step IV).

Sixty grams of the fraction obtained by Step IV were redissolved in the original 0.5M CaCl$_2$, 6M urea solution and dialyzed against 0.25M citrate buffer, pH 3.1, at 4° C. After 24 hours a grayish white precipitate was collected by centrifugation at 40,000 g for 1 hour. The precipitate was extensively washed, defatted in 1:1 chloroform-methanol, and evaporated to dryness (Step V).

Twenty-two grams of the fraction obtained by Step V were redissolved in 4M GuHCl and diluted about 4 times to about 1.5M GuHCl at 28° C. for 12 hours or until formation of a precipitate. The 1.5M GuHCl soluble fraction was washed, dialyzed against water for 24 hours, until precipitation was complete. The water insoluble precipitate was centrifuged, extensively washed in cold water, lyophilized and weighed (Step VI). The 1.5M GuHCl insoluble fraction was centrifuged at 50,000 g for 1 hour, washed in cold water, lyophilized, and weighed (Step VII).

The protein fraction obtained by Step VII was redissolved in 0.5M CaCl$_2$ in 6M urea, and dialyzed against 0.2% Triton X-100 in 0.10M Tris HCl buffer solution, pH 7.2, for 24 hours, at 28° C. The dialysis was continued for an additional 12 hours. (Step VIII).

The supernatant obtained in Step VIII was dialyzed against 0.1% Triton X-100 in 0.5M Tris HCl for 48 hours. This produced another precipitate, which after centrifugation at 50,000 g for 1 hour, washing and lyophilization, weighed 5.3 g (Step IX).

Table 4 summarizes nine steps for extracting BMP from bone by chemical solvents and differential precipitation.

In Steps I and II, 10 kgs. of pulverized chloroform methanol defatted bone produced three kilograms of pulverized fat free demineralized bone matrix. In Step III, 1.4 kgs. of insoluble bone matrix gelatin was obtained from 3 kgs. of demineralized whole bone matrix. Whole undemineralized and demineralized bone matrix particles induced little or no bone formation when implanted in muscle pouches in mice. Insoluble bone matrix gelatin, however, produced some very small deposits in less than half of the samples four weeks after implantation.

In Step IV, 60 grams of 0.5M CaCl$_2$, 6M urea soluble, 0.25M urea insoluble proteins were obtained from 1.4 kgs. of bone matrix gelatin; this protein fraction produced bone formation in 16/20 implants and the yield was three times greater in volume than the yield from bone matrix gelatin. In Step V, the gelatin peptides were separated from the 0.5M CaCl$_2$-6M urea soluble proteins by dialysis against 0.5M citrate buffer at pH 3.4. This reduced the quantity of protein with high BMP activity from 60 to 22 grams but further increased the incidence in yields of bone formation to 18/20 implants.

In Step VI, the precipitate obtained by Step V was solubilized in 4M GuHCl and dialyzed against 1.5M GuHCl until a precipitate formed. The supernatant, consisting of 1.5M GuHCl soluble protein, was dialyzed against water to obtain a precipitate weighing 7.23 grams. This 1.5M GuHCl soluble water insoluble fraction consisted of the following proteins with an apparent molecular weight of about 45-, 34-, 23-, 22-, three in the range of 17- to 18-, and two in the range of 12- to 14-kDa. Fraction VI produced bone formation in 27/30 implants.

In Step VII, the 1.5M GuHCl insoluble proteins were washed and lyophilized. The total weight of this fraction VII was 12 grams. The electrophoretic components were chiefly 34-, 22-, 17-, 12- and 5-kDa. Fraction VII induced scanty deposits of bone in 4/20 implants.

In Step VIII, in which fraction VI was redissolved in 4M GuHCl and then dialyzed against Triton X-100 the 34-kDa was removed along with several other proteins. The Triton X-100 insoluble proteins consisted chiefly of 22-, three 17- to 18-, and 14-kDa components with very small amounts of lower molecular weight proteins. After exhaustive washing in cold water and lyophilization, the fraction obtained by Step VIII weighed about 1.5 grams, and was reddish brown in color.

Step IX, consisting of Triton-X soluble components, chiefly the 34-kDa protein, contaminated with small amounts of 65-, 45-, 22-, and 12-kDa proteins, induced formation of fibrous connective tissue only.

The individual protein fractions were dialyzed against cold water to remove GuHCl and to precipitate the water insoluble proteins. Lyophilized weighed samples of each fraction were incubated for 24 hours in 0.1M sodium phosphate buffer containing 2M urea and 0.1% sodium dodecyl sulfate (SDS), pH 7.2, for polyacrylamide gel electrophoresis (PAGE); 5 $\mu$l (2.5 mg/ml) samples were applied to 8.5% gel, electrophoresed at 25 mA, and stained with 0.044% Coomassie brilliant blue R-250. The molecular weights were determined with the aid of two sets of low molecular weight standards (Pharmacia, Uppsala) with a range of 92- to 15.3-kDa, and another (BRL, Bethesda, MD) with a range of 43- to 3-kDa.

For preparative tube gel electrophoresis and amino acid analysis of individual proteins, 6-mm slabs and 1-cm tubes of 15% PA were loaded with a 0.2% SDS and 0.12% urea solution of hBMP; 1.7 µg/tube was run at 15 mA.tube for 18 hours. Gels were sliced with a knife across molecular weight zones corresponding to the 34-, 24-, 22-, 17.5, and 14-kDa protein using duplicates stained for orientation. Gel slices containing the 17.5-kDa bBMP were extracted with 0.2% SDS, dialyzed against water, and lyophilized; 200-ug samples were hydrolyzed under vacuum for 24 hours at 110° C., in 1.0 ml of 6N HCl, and applied to an amino-acid analyzer (equipped with a Spectrum Physics data reduction system). Similarly prepared 35-, 24, 22-, and 145-kDa protein fractions were analyzed for comparison.

TABLE 4

YIELD OF BMP COMPOSITION FROM BOVINE BONE*

| Step No. | Fraction | Weight | MW of the Major Electrophoretic Components, k | Incidence** | Yield*** mm³/mg |
|---|---|---|---|---|---|
| I | Wet bone, fresh, pulverized | 10.0 kg | — | 0/10 | 0 |
| II | Dry, fat free demineralized | 3.0 kg | — | 0/10 | 0 |
| III | Bone matrix gelatin | 1.4 kg | — | 5/10 | 0 |
| IV | 0.5 M CaCl$_2$-6.0 M urea soluble 0.25 urea insoluble | 60.0 g | — | 16/20 | 1.5 |
| V | 0.5 M CaCl$_2$, 6.0 M urea, dialyze against 0.25 M citrate buffer pH 3.1. Wash precipitate in water, centrifuge, redefat in 1.1 chloroform methanol. Evaporate to dryness. | 22.0 g | 18, 68, 45, 34 - 17-18 | 18/20 | 2.0 |
| VI | 4 M GuHCl soluble, 1.5 M GuHCl soluble, water insoluble | 7.23 g | 45, 34, 24, 22, 18-17, 14, 12 | 27/30 | 2.5 |
| VII | 1.5 M GuHCl insoluble | 12.0 g | 34, 22, 17 | 4/20 | 0.5 |
| VIII | 0.5 M CaCl$_2$, 60 M urea soluble, dialyze against 0.2% Triton x-100, 010 M Tris-HCl, pH 7.2 for 24 hours. Then dialyze 0.1% Triton X-100 in 0.5 M Tris, pH 7.2 for 12 hours until precipitation is complete. | 1.5 g | 22, 12-18, 14, 12, 5 | 58/60 | 8.0 |
| IX | Dialyze, supernatant against water, and lyophilize | 5.3 g | 65, 45, 34, 22, 12 | 0/10 | 0 |

*BMP Activity = .001% of wet bone.
**BMP Activity = .003% of demineralized lyophilized fat free bone matrix.
***Implants in rump of athymic or cortisone-immunosuppressed, or untreated mice, histomorphometric volume.

EXAMPLE 3

Hydroxyapatite (HA) columns of Bio-Gel HTP (Bio-Rad Laboratories, California), were prepared from 15 g./100 ml of 0.05M NaP$_i$/6M urea. After 10 minutes the solvent was decanted and the HA was resuspended to give a settled bed height of 9 cm (volume, approximately 55 ml). The column was equilibrated with 100 ml starting buffer (at a flow rate of 0.6 ml/min.) the flow rate of the column by gravity; 100 mg of the preparation obtained by Step VIII of Example 2 was dissolved in 6M urea, applied to the column, and separated into fractions. Each fraction was dialyzed against deionized water (cold), frozen and lyophilized. Weighed samples were incubated for 24 hours in 0.1M sodium phosphate buffer containing 2M urea and 0.1% SDS, pH 7.2, for (PAGE); 5 μl (2.5 mg/1 ml) of each sample were applied to 8.5% gel and electrophoresed at 25 mA, and stained with 0.044% Coomassie Brilliant Blue R-250. The electrophoretic mobilities were measured with the aid of two sets of standard proteins.

By means of HA chromatography, buffered 6M urea solutions of the proteins obtained from Step VIII three or four proteins in the molecular weight range of 17- to 18-kDa, were isolated from the 22-, 14-kDa and other proteins. Individual protein fractions were eluted using a gradient of 0.05 to 0.3M phosphate buffer at pH 7.3. A 22-kDa and some other proteins lacking BMP activity were reddish brown in color, and recovered in solutions of phosphate ions ranging from 0.05 to 0.01M in concentration. Components possessing BMP activity was present in proteins afterwards eluted with 0.3 to 0.4M phosphate buffer. Fractions containing 3 components, in the range of 17- to 18-kDa (with traces of 14-kDa and 22-kDa proteins) were generally eluted at concentrations of phosphate buffer of 0.18 to 2.0M. By re-chromatographing this fraction it was possible to purify each of the three with varying proportions of contamination with 14-kDa and other low molecular weight proteins.

The protein consistently associated with BMP activity was white in color and fluffy in texture with an apparent molecular weight of 18.5±0.5-kDa. Two other proteins with molecular weights of 17.5 and 17.0-kDa did not induce bone formation.

EXAMPLE 4

The individual proteins isolated by preparative gel electrophoresis were hydrolyzed at 110° C. for 24 or 72 hours. in 6M HCl in evacuated sealed tubes. Analysis for tryptophan and cysteine were performed following hydrolysis at 110° C. for 24 hours in 2.5M KOH. Amino acid analysis was performed on an amino acid analyzer (Beckman 119 C) equipped with a Spectra Physics 4000 data reduction system.

EXAMPLE 5

BMP activity was determined by implantation of isolated protein fractions and individual proteins in the hindquarter muscles of Swiss-Webster strain mice and skull trephine defects in monkeys, dogs, and rats. The implants (xenogeneic) were excised 21 days after the operation, and examined by micro-radiographic and histologic methods. Histologic sections were stained in hematoxylin and eosin and azure II.

EXAMPLE 6

A protein and protein aggregate with high BMP activity, obtained by Step VIII, are soluble only in 6 to 8M urea or 4M GuHCl and insoluble in water. The BMP and associated proteins became soluble in water after large quantities of the 14k component (but not all of the 14-kDa and some lower molecular weight proteins) were removed by ultrafiltration of a 6M urea solution.

The Triton X-100 soluble, 34-kDa protein (isolated by Step IX) was the single most abundant non collagenous protein of the group lacking BMP activity.

Analyses of the samples of 22-, 18.5±0.5-kDa, and 14-kDa bovine BMP fractions, isolated by elution of SDS PAGE disc gel slices had the composition of an acidic polypeptide, and are shown in Table 2. Not shown in Table 2, is 1 residue of hydroxyproline and three residues of gla in the 18.5±0.5-kDa protein.

EXAMPLE 7

When the 18.5±0.5-kDa bBMP factor was present, implants of protein fractions isolated by hydroxyapatite chromatography induced bone formation in the mouse hind quarter muscles, and produced regeneration in trephine defects in rat and dog skulls. Implants of 10 mg or more of 14-, 17.5-, 17.0-, 22-, or 34-kDa proteins alone, or in various combinations failed to induce bone formation. The association with the 14-kDa decreased solubility in vitro, increased resorption time in vivo and improved both incidence and the yield of new bone from implants of as little as 1 mg. Implants of 34-kDa combinations with 17.5-kDa did not improve and may even have suppressed the bone formation. Implants of 7 parts 22-kDa, 2 parts 18.5±0.5-kDa and 1 part 14-kDa weighing 3 mg consistently induced formation of large deposits of bone.

Almost unlimited quantities of BMP factor could be purified by antibody-affinity chromatography or by recombinant-DNA technology.

It will be understood that it is intended to cover all changes and modifications of the examples of the invention herein chosen for the purpose of illustration which do not constitute departures from the spirit and scope of the invention.

I claim:

1. Substantially pure bone morphogenetic protein composition comprising BMP factor and at least one BMP associated protein selected from a group consisting of BMP associated proteins having molecular weights in the range of between about 14 dKa and about 34 kDa, said BMP factor being capable of inducing bone formation independent of the presence of said BMP associated proteins, and said BMP associated proteins being incapable of inducing bone formation independent of the presence of said BMP factor.

2. The bone morphogenetic protein composition of claim 1, wherein the BMP factor is human BMP factor having a molecular weight of 17.5±0.5 dKa, and the BMP associated proteins are human BMP associated proteins having molecular weights of about 14-, 22-, 24- and 34-kDa.

3. The bone morphogenetic protein composition of claim 1, wherein the BMP factor is bovine BMP factor having a molecular weight of 18.5±0.5 kDa, and the BMP associated proteins are bovine BMP associated proteins having molecular weights of about 14-, 16.5-, 17-, 17.5, 22-, 24-, and 34-dKa.

4. The aggregate of:
   (a) hBMP factor having a molecular weight in the range of about 17.5±0.5 kDa, and comprised, as determined by amino acid analysis, of lysine, histidine, arginine, aspartate, threonine, serine, glutamate proline, glycine, alanine, cystine, leucine, tyrosine and phenylalanine; and (b) at least one BMP-associated protein selected from a group consisting of BMP-associated proteins having molecular weights of about 14-, 22-, 24-, and 34-kDa.

5. The aggregate of:
(a) bBMP factor having a molecular weight in the range of about 18.5±0.5 kDa and and comprised, as determined by amino acid analysis, of lysine, histidine, arginine, aspartate, threonine, serine, glutamate, proline, glycine, alanine, valine, methionine, isoleucine, leucine, tyrosine, and phenylalanine; and
(b) at least one BMP associated protein selected from a group consisting of BMP associated proteins having molecular weights of about 14-, 16.5-, 17.0-, 22-, 24-, and 34-kDa.

6. The aggregate of claim 5 consisting essentially of about 7 parts 22-kDa and about 1 part 14-kDa BMP associated proteins, and about 2 parts 18.5±0.5-kDa bBMP factor.

7. The aggregate of hBMP factor and 14-kDa protein of claim 4 wherein said aggregate is insoluble in 0.6 N HCl, soluble in 6M urea, soluble in 4M guanidine HCl; soluble in 0.1% SDS, soluble in 0.02N HCl and partially soluble in ethylene glycol.

8. The aggregate of claim 4, wherein said hBMP factor, as determined by amino acid analysis, is comprised, in approximate mole percentages, of lysine 4%; histidine, 1.5%; arginine, 7%; aspartate, 8%; threonine, 3%; serine, 8%; glutamate 10%; proline, 3.5%; glycine, 25%; alanine, 7%; cystine, 3%; leucine, 7%; tyrosine, 3%; phenylalanine, 2.5%; and about 3 residues/170 residues carboxyglutamic acid.

9. The aggregate of claim 8, said hBMP factor having a molecular weight in the range of about 17.5±0.5 kDa and being trypsin and chymotrypsin labile, alkali sensitive, partially degradable by pepsin and papain, and resistant to chondroitinases A, B and C; amylase; neuroamidase; hyaluronidase; alkaline phosphates; acid phosphatase; chymopapain; collagenase; tyrosinase; thermolysine; RNase and DNase.

10. The aggregate of claim 9, said hBMP factor having a molecular weight of about 17.5±0.5 kDa and being an acidic polypeptide, bindable to hydroxyapetite, having an isoelectric point of 5.0±0.2, being insoluble in chloroform, methanol, absolute alcohol, and acetone and being degraded by acid alcohol solutions.

11. The aggregate of claim 5, wherein said bBMP factor, as determined by amino acid analysis, is comprised, in approximate mole percentages, of lysine, 10%; histidine, 3.5%; arginine, 16.5%; aspartate, 16.5% threonine, 7%, serine, 17.5%; glutamate, 23.5% proline, 9% glycine, 12.5%; alanine, 14.5%; valine, 11%; methionine, 2.5%; isoleucine, 6%; leucine, 15%; tyrosine, 8%; phenylalanine, 7%.

12. The aggregate of claim 5, wherein said 22 kDa protein is comprised, in approximate mole percentages, of lysine, 2.5%; histidine, 2.5%, arginine, 6%; aspartate, 12.5%; threonine, 3.5%; serine, 5.5%; glutamate, 14.5%; proline, 6.5%; glycine, 8.5%; alanine, 6%; cystine, 3.5%; valine, 4.5%; methionine, 2%; isoleucine, 2.5%; leucine, 6.5%; tyrosine, 8.5%; and phenylalanine, 4%.

13. The aggregate of claim 5, wherein said 14-dKa protein is comprised, in approximate mole percentages, of lysine, 4.5%; histidine, 1.5%; arginine, 9%; aspartate, 11.5%; threonine, 2.5%; serine, 6.5%; glutamate, 15%; proline, 5%; glycine, 6% alanine, 8.5%; cystine, 2%; valine, 4%; methionine, 1.5%; isoleucine, 4%; leucine, 7.5%; tyrosine, 6.5%; and phenylalanine, 4%.

* * * * *